(12) United States Patent
Mannari

(10) Patent No.: US 10,118,986 B2
(45) Date of Patent: Nov. 6, 2018

(54) CORROSION-RESISTANT COATINGS AND METHODS USING POLYEPDXYSILANE PRECURSORS

(71) Applicant: EASTERN MICHIGAN UNIVERSITY, Ypsilanti, MI (US)

(72) Inventor: Vijaykumar M. Mannari, Saline, MI (US)

(73) Assignee: EASTERN MICHIGAN UNIVERSITY, Ypsilanti, MI (US)

( * ) Notice: Subject to any disclaimer, the term of this patent is extended or adjusted under 35 U.S.C. 154(b) by 810 days.

(21) Appl. No.: 14/203,075

(22) Filed: Mar. 10, 2014

(65) Prior Publication Data

US 2014/0272420 A1   Sep. 18, 2014

Related U.S. Application Data

(60) Provisional application No. 61/777,132, filed on Mar. 12, 2013.

(51) Int. Cl.
| | |
|---|---|
| *C07F 7/18* | (2006.01) |
| *C08G 59/14* | (2006.01) |
| *C08G 59/50* | (2006.01) |

(52) U.S. Cl.
CPC ............. *C08G 59/14* (2013.01); *C07F 7/18* (2013.01); *C07F 7/1804* (2013.01);
(Continued)

(58) Field of Classification Search
CPC ......... C08G 59/14; C08G 59/504; C07F 7/18; C07F 7/1804
See application file for complete search history.

(56) References Cited

U.S. PATENT DOCUMENTS

| | | | | |
|---|---|---|---|---|
| 5,543,445 A | * | 8/1996 | Nield ................ | C08F 290/064 523/406 |
| 2008/0009562 A1 | * | 1/2008 | Mitachi .............. | C08G 59/4085 523/176 |

(Continued)

OTHER PUBLICATIONS

Niknahad M., and Mannari. V., "Sol-gel Derived Organic-Inorganic Hybrid Chromate-Free Pretreatment for Industrial Aluminum Alloys," poster presentation at CoatingsTech Conference 2013, Chicago, Illinois (Mar. 12, 2013).

*Primary Examiner* — Ling Siu Choi
*Assistant Examiner* — David L Miller
(74) *Attorney, Agent, or Firm* — Marshall, Gerstein & Borun LLP

(57) ABSTRACT

The disclosure relates to curable polyepoxysilane compounds and compositions, methods related to curing of such compounds via hydrolysis and/or condensation to form coatings on a substrate, and coated articles formed from the curable polyepoxysilane compounds. The polyepoxysilane compounds are silane-functional precursors and can be used as coatings (or pretreatments) on various substrates (e.g., metals such as aluminum) and provide a substantial improvement in corrosion resistance relative to other anti-corrosion coatings. The silane-functional precursors can be prepared by reaction of functional silanes (e.g., amino-functional silanes or other epoxide-reactive functionalized silanes) with epoxide-containing organic or hydrocarbon compounds and oligomers/polymers thereof (e.g., glycidyl-type ethers or other epoxide-/oxirane-functionalized hydrocarbon compounds), for example including hydrocarbons with one or more aromatic hydrocarbon groups (e.g., in an aromatic polyether).

13 Claims, 3 Drawing Sheets

(52) U.S. Cl.
CPC ..... *C08G 59/504* (2013.01); *Y10T 428/31515* (2015.04); *Y10T 428/31529* (2015.04)

(56) References Cited

U.S. PATENT DOCUMENTS

2009/0104464 A1* 4/2009 Galbo ................... C07C 59/90
428/461
2012/0258319 A1 10/2012 Mannari

* cited by examiner diglycidylether of bisphenol-A (DGEBA)

bis(trimethoxysilylpropyl)amine (BTMSPA)

aminopropyltrimethoxy silane (APTMS)

isophorone diisocyanate (IPDI)

glycidoxypropyl tri(m)ethoxy silane (GPTMS/GPTES).

glycidyl ether of para-tertiary butyl phenol (GEPTBP)

US 10,118,986 B2

CORROSION-RESISTANT COATINGS AND METHODS USING POLYEPDXYSILANE PRECURSORS

CROSS REFERENCE TO RELATED APPLICATION

Priority is claimed to U.S. Provisional Application No. 61/777,132 (filed on Mar. 12, 2013), which is incorporated herein by reference in its entirety.

STATEMENT OF GOVERNMENT INTEREST

None.

BACKGROUND OF THE DISCLOSURE

Field of the Disclosure

The disclosure relates to curable polyepoxysilane compounds and compositions methods related to curing of such compounds via hydrolysis and/or condensation to form coatings on a substrate, and coated articles formed from the curable polyepoxysilane compounds.

Brief Description of Related Technology

Aluminum and aluminum alloys (AA) are important materials, mainly for aerospace applications among many others. Protection of aluminum-based materials from atmospheric corrosion is important for long term durability and costs associated with their maintenance. Aircraft coatings are designed to provide long-lasting corrosion and abrasion protection in addition to decorative functions. The coating system is typically comprised of a conversion coating layer, a primer layer, and a topcoat layer.

A conversion coating is a type of coating deposited at the metal surface such that it is strongly adherent and covalently bonded to the surface, thus providing excellent adhesion and a barrier for corrosive elements. Additionally, it provides for good adhesion of the primer layer to its surface. Thus, conversion coatings (surface pretreatments) have an important role in the success of a composite coating system such as used for aircraft.

Among available technologies for surface pretreatments, chromate conversion coatings are by far the most efficient for aluminum and alloys. These coatings are typically applied from acidic mixtures of soluble hexavalent chromium salts by oxidation-reduction reactions with the metal surface. A continuous layer of insoluble trivalent chromium and soluble hexavalent chromium compounds are formed. The use of chromates in the coating has generated serious environmental and health issues for the coating industry because hexavalent chromates are carcinogenic and highly toxic. The costs associated with worker safety and the containment, treatment, and disposal of hazardous materials related to the coating process is one of the highest costs for maintenance activities in the Air Force. Recent legislation, however, substantially limits the use of chromate-based coatings.

SUMMARY

The disclosure relates to curable polyepoxysilane compounds and compositions, methods related to curing of such compounds via hydrolysis and/or condensation to form coatings on a substrate, and coated articles formed from the curable polyepoxysilane compounds. The polyepoxysilane compounds are silane-functional precursors and can be used as coatings (or pretreatments) on various substrates (e.g., metals such as aluminum) and provide a substantial improvement in corrosion resistance relative to other anti-corrosion coatings. The silane-functional precursors can be prepared by reaction of functional silanes (e.g., amino-functional silanes or other epoxide-reactive functionalized silanes) with epoxide-containing organic or hydrocarbon compounds and oligomers/polymers thereof (e.g., glycidyl-type ethers or other epoxide-/oxirane-functionalized hydrocarbon compounds), for example including hydrocarbons with one or more aromatic hydrocarbon groups (e.g., in an aromatic polyether).

In one aspect, the disclosure relates to a curable polyepoxysilane compound comprising: (a) a hydrocarbon moiety comprising at least 1 epoxy group (e.g., 1, 2, 3, or 4, epoxy groups, for example at least 1, 2, 3, 4, or more epoxy groups) bonded thereto; and (b) at least 3 hydrolysable silyl groups (e.g., at least 3, 4, 6, 9, 12, or more hydrolysable silyl groups) linked to the hydrocarbon moiety via the at least one epoxy group. For example, the curable polyepoxysilane compound can be generally represented by $R_H$—[—CH(OH)—CH$_2$—R$_S$]$_x$ or $R_H$—[—CH$_2$—CH(OH)—R$_S$]$_x$, where $R_H$ represents the hydrocarbon moiety (e.g., comprising one, two, or more aromatic hydrocarbon groups such as substituted or unsubstituted phenolic ether residues) of the curable polyepoxysilane compound and the eventual cured network polymer, —CH(OH)—CH$_2$— and —CH$_2$—CH(OH)— represent the epoxy linking group(s), $R_S$ represents a functional group including one or more hydrolysable silyl groups (e.g., alkoxysilylalkyl groups including a functional group (such as an amino group) linking to the epoxy groups), and x is at least one (e.g., x is 1, 2, 3, or 4, for example at least 1, 2, 3, or 4 and/or up to 6, 8, 10, 12, or 20, where x can represent the number of epoxy groups in the curable polyepoxysilane compound).

In another aspect, the disclosure relates to a process for curing a curable polyepoxysilane compound, the process comprising: (a) providing a curable polyepoxysilane compound according to any of the variously disclosed embodiments; and (b) curing the curable polyepoxysilane compound with water, thereby hydrolyzing and condensing at least some of the hydrolysable silyl groups to form a cured polyepoxysilane compound comprising covalent intermolecular siloxane crosslinks in the cured polyepoxysilane compound. In a refinement, providing the curable polyepoxysilane compound in part (a) comprises providing a mixture comprising: (i) the curable polyepoxysilane compound, (ii) an organic solvent for the curable polyepoxysilane compound, (iii) water, (iv) a catalyst, (v) optionally a corrosion inhibitor; and (vi) optionally a silane crosslinker. In another refinement, the process further comprises: (c) applying partially cured polyepoxysilane compound (e.g., at least partially hydrolyzed, at least partially condensed, or both) from part (b) to a substrate; and (d) further curing the partially cured polyepoxysilane compound on the substrate, thereby forming the cured polyepoxysilane compound as a coating on the substrate. In another refinement, the curable polyepoxysilane compound is the only source of intermolecular siloxane crosslinks the cured polyepoxysilane compound.

Various refinements and extensions of the disclosed curable polyepoxysilane compounds, compositions, and related processes are possible. For example, the hydrolysable silyl groups can be selected from the group consisting of methoxy groups, ethoxy groups, propoxy groups, isopropoxy groups, and combinations thereof bound to one or more silicon atoms (e.g., two or more silicon atoms). In an embodiment, the curable polyepoxysilane compound has a number of hydrolysable silyl groups of at least 3, 4, 6, 9, or 12 and/or up to 6, 9, 12, 18, or 24 (e.g., ranging from 6, 9, or 12 to 24).

The hydrocarbon groups/moieties in the various components of the curable polyepoxysilane compound generally can include saturated or unsaturated, linear or branched aliphatic hydrocarbon groups, alicyclic hydrocarbon groups, aryl/aromatic hydrocarbon groups, and heteroatom-including analogs/derivatives of the same (e.g., including N, O, S heteroatoms). In an embodiment, the hydrocarbon moiety has a structure corresponding to a reaction product resulting from an amination reaction of a glycidyl-hydrocarbon ether with an aminosilane. Alternatively or additionally, the hydrocarbon moiety can more generally result from/be represented by a reaction product of the glycidyl- (or other epoxide-functional-) hydrocarbon ether with a functionalized silane having an epoxide-reactive functional group (e.g., at a terminal end of an aliphatic hydrocarbon chain having silane functionality/hydrolysable silyl groups at an opposing end), such as amines (primary, secondary amino groups), alcohols and phenols (aliphatic and aromatic —OH groups), thiols (—SH groups), carboxylic acids/anhydrides, and other epoxide groups (e.g., generally analogous to suitable amino silanes, but with different epoxide-reactive linking groups as noted). In a refinement, (i) the glycidyl-hydrocarbon ether is represented by

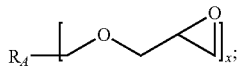

(ii) $R_A$ is an aromatic hydrocarbon moiety comprising one or more aromatic hydrocarbon groups (e.g., as described below); and (iii) x is at least one (e.g., x is 1, 2, 3, or 4, for example at least 1, 2, 3, or 4 and/or up to 6, 8, 10, 12, or 20). Alternatively or additionally, the hydrocarbon moiety comprises one or more aromatic hydrocarbon groups, for example $C_6$-substituted or unsubstituted aromatic groups such as substituted or unsubstituted phenolic residues or ethers thereof (such as present in a glycidyl- or other epoxide-functional phenolic ether precursor to the curable polyepoxysilane compound). As representative examples, the aromatic hydrocarbon groups can include any of a variety of bisphenol-based moieties represented by $R_B$—[—Ph]$_2$, where $R_B$ is a hydrocarbon or heteroatom-substituted hydrocarbon linking group (such as having 1 to 50 carbons) between two Ph groups representing phenolic residues or ethers thereof. Representative (aromatic)bisphenol moieties includes derived from any commonly known bisphenol compound, such as bisphenol A, AP, AF, B, BP, C (cresol-based), C (chlorinated), E, F, G, M, S, P, PH, TMC, and/or Z. The hydrocarbon moiety additionally can include a plurality of aromatic hydrocarbon groups such as from bisphenol-based oligomers or polymers (e.g., having a plurality of $C_6$ aromatic groups as part of the backbone and/or as pendent groups, such as part of an aromatic/aliphatic polyether in a bisphenol-diglycidyl ether epoxy resin/prepolymer for silane functionalization to form the curable polyepoxysilane compound) or other phenol-based resins such as phenol-formaldehyde resins.

In another refinement, (i) the curable polyepoxysilane compound comprises a compound having the formula (I):

R—[—O—R$_4$—CH(OH)—CH$_2$—NA$_1$A$_2$]$_x$;  (I)

(ii) R is selected from the group consisting of hydrocarbons containing from 1 to 50 carbon atoms and heteroatom-substituted hydrocarbons containing from 1 to 50 carbon atoms (e.g., aromatic and/or aromatic group-containing hydrocarbons); (iii) A$_1$ is represented by —R$_1$—Si(R$_3$)$_{3-y}$X$_y$; (iv) A$_2$ is represented by —R$_2$—Si(R$_3$)$_{3-z}$X$_z$, or H or R$_3$; (v) X is a hydrolysable group independently selected from the group consisting of alkoxy groups, aryloxy groups, carboxyloxy groups, and halogens; (vi) R$_1$ and R$_2$ are independently selected from the group consisting of hydrocarbons containing from 1 to 20 carbon atoms and heteroatom-substituted hydrocarbons containing from 1 to 20 carbon atoms; (vii) R$_3$ is independently selected from the group consisting of H, hydrocarbons containing from 1 to 20 carbon atoms, and heteroatom-substituted hydrocarbons containing from 1 to 20 carbon atoms; (viii) R$_4$ is either (A) absent (e.g., reflecting a direct link between the ether oxygen atom and the ring-opened epoxy group) or (B) selected from the group consisting of hydrocarbons containing from 1 to 20 carbon atoms and heteroatom-substituted hydrocarbons containing from 1 to 20 carbon atoms; (ix) x is at least one (e.g., x is 1, 2, 3, or 4, for example at least 1, 2, 3, or 4 and/or up to 6, 8, 10, 12, or 20); (x) y is 1, 2, or 3; (xi) z is 1, 2, or 3 when A$_2$ is not H or R$_3$; and (xii) the number of hydrolysable groups X is at least 3 (e.g., at least 3, 4, 6, 9, or 12 and/or up to 6, 9, 12, 18, or 24). Alternatively or additionally, the curable polyepoxysilane compound can comprise a compound having the formula (II) (e.g., representing an alternative position of the epoxy hydroxy group resulting from the epoxide ring-opening reaction with a hydrocarbon moiety precursor and an aminosilane):

R—[—O—R$_4$—CH$_2$—CH(OH)—NA$_1$A$_2$]$_x$  (II)

In a further refinement of the compound of formula I or II, (i) A$_1$ is represented by —C$_3$H$_6$—Si(OCH$_3$)$_3$ or —C$_3$H$_6$—Si(OC$_2$H$_5$)$_3$; (ii) A$_2$ is represented by H; and (iii) R$_4$ is present and is represented by —CH$_2$—. In yet a further refinement of the compound of formula I or II, (i) A$_1$ is represented by —C$_3$H$_6$—Si(OCH$_3$)$_3$ or —C$_3$H$_6$—Si(OC$_2$H$_5$)$_3$; (ii) A$_2$ is represented by —C$_3$H$_6$—Si(OCH$_3$)$_3$ or —C$_3$H$_6$—Si(OC$_2$H$_5$)$_3$; and (iii) R$_4$ is present and is represented by —CH$_2$—.

In another aspect, the disclosure relates to a coated composite article comprising: (a) a substrate; and (b) a cured polyepoxysilane compound as a coating on a surface of the substrate, the cured polyepoxysilane compound coating comprising the hydrolysis and condensation reaction product of (i) a curable polyepoxysilane compound according to any of the variously disclosed embodiments, and (ii) water; wherein: (i) at least some of the hydrolysable silyl groups of the curable polyepoxysilane compound have been hydrolyzed with the water and condensed, thereby forming covalent intermolecular siloxane crosslinks between curable polyepoxysilane compound molecules in the cured polyepoxysilane compound coating; (ii) the cured polyepoxysilane compound coating is sufficiently crosslinked with the intermolecular siloxane crosslinks to form a networked polymer; and (iii) optionally the curable polyepoxysilane compound is the only source of intermolecular siloxane crosslinks the cured polyepoxysilane compound coating.

Various refinements and extensions of the foregoing coated composite articles are possible. For example, the substrate can be a metallic substrate and the cured polyepoxysilane compound coating can reduce or prevent corrosion of the metallic substrate (e.g., comprising aluminum such as elemental aluminum or an aluminum alloy). In a refinement, the cured polyepoxysilane compound coating can be covalently bonded to the metallic substrate via a —SiO— functional group. In another refinement, the coated article further comprises: (c) optionally a polymeric primer as a coating on a surface of the cured polyepoxysilane compound opposite the substrate; and (d) a polymeric topcoat as a coating on a surface of the polyurethane primer (when present) opposite the cured polyepoxysilane compound or on a surface of the cured polyepoxysilane compound opposite the substrate (when no primer is present). In another refinement, the cured polyepoxysilane compound coating further comprises a corrosion inhibitor selected from the group consisting of 8-hydroxyquinoline, benzimidazole, mercaptobenzothiazole, mercaptobenzimidazole, and combinations thereof.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

Figure 1:
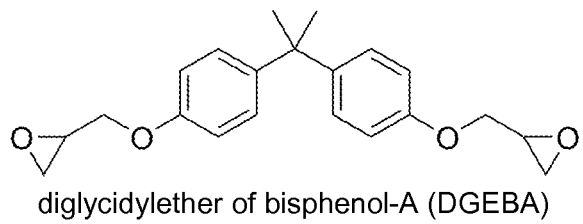
FIG. 1 illustrates chemical structures of representative amino silanes, epoxide-containing hydrocarbon compounds, and isocyanate compounds.
Figure 1:
Figure 1:
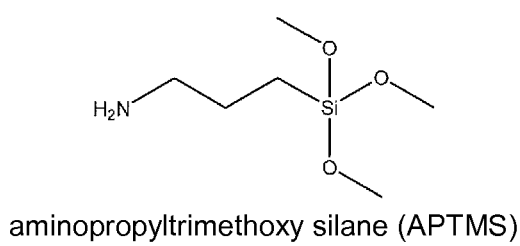
Figure 1:
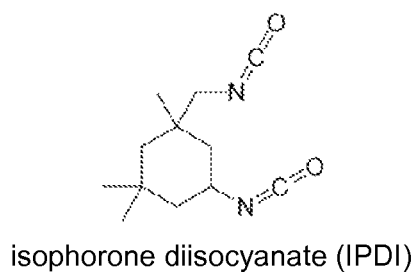
Figure 1:
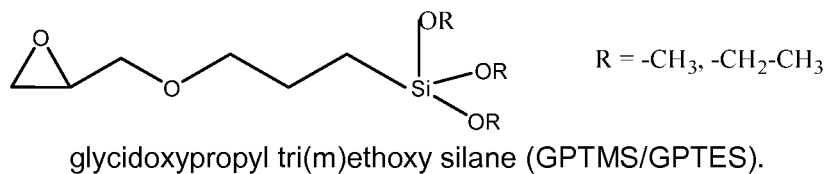
Figure 1:
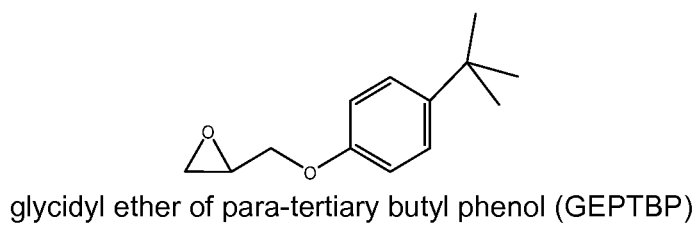

While the disclosed compounds, compositions, articles, and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The disclosure relates to curable polyepoxysilane compounds and compositions, methods related to curing of such compounds via hydrolysis and/or condensation to form coatings on a substrate, and coated articles formed from the curable polyepoxysilane compounds. The polyepoxysilane compounds are silane-functional precursors and can be used as coatings (or pretreatments) on various substrates (e.g., metals such as aluminum) and provide a substantial improvement in corrosion resistance relative to other anti-corrosion coatings. The silane-functional precursors can be prepared by reaction of functional silanes (e.g., amino-functional silanes or other epoxide-reactive functionalized silanes) with epoxide-containing organic or hydrocarbon compounds and oligomers/polymers thereof (e.g., glycidyl-type ethers or other epoxide-/oxirane-functionalized hydrocarbon compounds), for example including hydrocarbons with one or more aromatic hydrocarbon groups (e.g., in an aromatic polyether).

Suitable amino silanes include those having at least one amine hydrogen atom and having at least one alkoxy silane group (e.g., methoxy, ethoxy, propoxy, isopropoxy, and combinations thereof for multiple alkoxy groups), for example including a linear or branched aliphatic hydrocarbon chain with a primary or secondary amino group (e.g., —NH$_2$ or —NH—) and with one or more alkoxy silane groups (e.g., —SiH$_{3-x}$(OR)$_x$ for x=1 to 3 and various alkyl R groups) suitably positioned at terminal chain or branch locations of the aliphatic hydrocarbon and separated from the amino group. Specific examples of suitable aminosilanes include (3-aminopropyl)trialkoxysilane (e.g., including trimethoxy (APTMS) and triethoxy (APTES) species) and bis(3-trialkoxysilylpropyl)amine (e.g., including trimethoxy (BTMSPA) and triethoxy (BTESPA) species). Alternative functional silanes analogous to the amino silanes can be used (e.g., where the amino group is replaced with another epoxide-reactive group such as an alcohol, phenol, thiol, carboxylic acid/anhydride, or other epoxide group).

Suitable epoxide-containing hydrocarbon compounds include glycidyl ethers of various hydrocarbon and heteroatom-substituted hydrocarbon groups, in particular aromatic hydrocarbons groups such as phenolic groups (e.g., where the phenolic —OH groups provide the reactive site for glycidyl ether formation with epichlorohydrin or other suitable epoxide precursor to provide a phenolic/aromatic ether character to the backbone of the curable polyepoxysilane compound or corresponding cured compound). Example epoxide-containing compounds include (but are not limited to) diglycidyl ether of bisphenol-A (DGEBA) (also known as liquid epoxy resin) or other general bisphenols, bisphenol-A based epoxy resins with varying epoxy equivalent weight (e.g., curable DGEBA oligomers of varying length), epoxy resins based on bisphenol-F (or other general bisphenols) with varying epoxy equivalent weight (e.g., curable oligomers of varying weight based on other bisphenols), and phenol-formaldehyde (e.g., novolac) type epoxy resins with varying molecular weight (e.g., glycidyl ether of a general phenol-formaldehyde resin).

FIG. 1 illustrates chemical structures of representative amino silanes and epoxide-containing hydrocarbon compounds according to the disclosure as well as an isocyanate precursor useful for forming comparative polyureasil curable compounds.

Curable Polyepoxysilane Compound

A curable polyepoxysilane compound according to the disclosure includes a hydrocarbon moiety with at least 1 epoxy group (e.g., 1, 2, 3, or 4, epoxy groups, for example at least 1, 2, 3, 4, or more epoxy groups) and at least 3 hydrolysable silyl groups (e.g., at least 3, 4, 6, 9, 12, or more hydrolysable silyl groups) linked to the hydrocarbon moiety via the at least 1 epoxy group. For example, the curable polyepoxysilane compound can be generally represented by R$_H$—[—CH(OH)—CH$_2$—R$_S$]$_x$ or R$_H$—[—CH$_2$—CH(OH)—R$_S$]$_x$. R$_H$ represents the hydrocarbon moiety of the curable polyepoxysilane compound and the eventual cured network polymer, for example including hydrocarbon and heteroatom-substituted hydrocarbon groups, including saturated or unsaturated, linear or branched aliphatic hydrocarbon groups, alicyclic hydrocarbon groups, aryl/aromatic hydrocarbon groups (e.g., one, two, or more aromatic hydrocarbon groups such as substituted or unsubstituted phenolic ether residues), and heteroatom-including analogs/derivatives of the same (e.g., including N, O, S heteroatoms). The epoxy linking groups are represented by —CH(OH)—CH$_2$— and —CH$_2$—CH(OH)— (e.g., depending on the particular epoxide ring-opening reaction product formed when forming the bond to R$_S$). R$_S$ represents a functional group including one or more hydrolysable silyl groups (e.g., alkoxysilylalkyl groups including a functional group (such as an amino group) linking to the epoxy groups. The value x is at least one (e.g., x is 1, 2, 3, or 4, for example at least 1, 2, 3, or 4 and/or up to 6, 8, 10, 12, or 20), and x can represent the number of epoxy groups in the curable polyepoxysilane compound.

The hydrolysable silyl groups include functional groups attached to a silicon atom (e.g., 1, 2, or 3 functional hydrolysable silyl groups per silicon atom) that can be hydrolyzed under suitable conditions (e.g., when in contact with water, such as under acidic conditions) to form corresponding silanol (Si—OH) functional groups, which in turn can be condensed to form siloxane (Si—O—Si) functional groups/linkages in a cured polyepoxysilane compound coating. The hydrolysable silyl group can include a hydrocarbon group linked via an oxygen atom to a silicon atom (e.g., Si—OR, such as alkoxy groups having 1, 2, 3, or 4 carbon atoms) and/or a halogen atom linked to a silicon atom (e.g., Si—X, such as for F, Cl, Br, or I). Examples of specific hydrolysable silyl groups include silicon-bound methoxy groups and/or ethoxy groups. The hydrolysable silyl groups are generally all the same to promote a uniform rate of hydrolysis/condensation, but the specific groups can be different in an embodiment if desired to have a distribution of different hydrolysis/condensation rates (e.g., a curable polyepoxysilane compound including some methoxy groups and some ethoxy groups). In different embodiments, the curable polyepoxysilane compound can include at least 3, 4, 6, 7, 8, 9, 12 and/or up to 12, 18, or 24 hydrolysable silyl groups, depending on the number of silicon atoms included and the degree of functionality of each silicon atom.

In an embodiment, the curable polyepoxysilane compound can be represented by the following Structure (I):

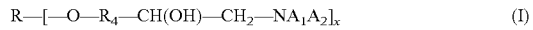

In Structure I, (a) R can be a hydrocarbon moiety or a heteroatom-substituted hydrocarbon moiety (e.g., N, O, S substituted) containing from 1 to 50 carbon atoms (e.g., at least 2, 4, 8, or 12 and/or up to 20, 30, 40, or 50 carbon atoms; aromatic and/or aromatic group-containing hydrocarbons); (b) $A_1$ contains hydrolysable silyl groups and can be represented by —$R_1$—Si($R_3$)$_{3-y}$$X_y$; (c) $A_2$ can contain hydrolysable silyl groups and can be represented by —$R_2$—Si($R_3$)$_{3-z}$$X_z$, or H or $R_3$; (d) X can be a hydrolysable group such as an alkoxy group, an aryloxy group, a carboxyloxy group, and a halogen (e.g., having at least having 1, 2, 3, or 4 and/or up to 4, 6, 8, 10, or 12 carbon atoms for non-halogens, where X can be the same or different on any particular silicon atom); (e) $R_1$ and $R_2$ can be a hydrocarbon moiety or a heteroatom-substituted hydrocarbon moiety (e.g., N, O, S substituted) containing from 1 to 20 carbon atoms (e.g., at least 2, 4, 8, or 12 and/or up to 4, 8, 12, 16, or 20 carbon atoms, where $R_1$ and $R_2$ can be the same or different); (f) $R_3$ can be hydrogen or a hydrocarbon moiety or a heteroatom-substituted hydrocarbon moiety (e.g., N, O, S substituted) containing from 1 to 20 carbon atoms (e.g., at least 2, 4, 8, or 12 and/or up to 4, 8, 12, 16, or 20 carbon atoms); and (g) $R_4$ can be either (A) absent (e.g., reflecting a direct link between the ether oxygen atom and the ring-opened epoxy group) or (B) a hydrocarbon moiety or a heteroatom-substituted hydrocarbon moiety (e.g., N, O, S substituted) containing from 1 to 20 carbon atoms (e.g., at least 2, 4, 8, or 12 and/or up to 4, 8, 12, 16, or 20 carbon atoms). $R_3$ can be selected in its various instances (e.g., explicitly illustrated in Structure I or as a component of $A_1$ or $A_2$) to be the same or different. The value x corresponds to the number of epoxy groups in the curable polyepoxysilane compound and can be 1, 2, 3, or 4, for example at least 1, 2, 3, or 4 and/or up to 6, 8, 10, 12, or 20. The specific selections for $R_1$-$R_4$, $A_1$, $A_2$, and X can be the same or different in each of the "x" instances of the epoxy-containing group of Structure I (e.g., for x=2 or higher, the substituents in the repeated unit [—O—$R_4$—CH(OH)—$CH_2$—$NA_1A_2$] can be the same or different). The values y and z correspond to the number of hydrolysable silyl groups in $A_1$ or $A_2$ (i.e., when $A_2$ is not H or $R_3$), respectively, and they independently can be 1, 2, or 3. The number of hydrolysable groups X in the curable polyepoxysilane compound is at least 3 (e.g., at least 3, 4, 6, 9, or 12 and/or up to 6, 9, 12, 18, or 24), for example being reflected by the product (x)(y) or (x)(y+z). Alternatively or additionally, the curable polyepoxysilane compound can be represented by the following Structure (II) (e.g., representing an alternative position of the epoxy hydroxy group resulting from the epoxide ring-opening reaction with a hydrocarbon moiety precursor and an aminosilane, where the other components are as otherwise indicated above for Structure I):

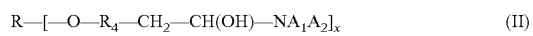

In a further refinement of the compound of Structure I or II, (i) $A_1$ is represented by —$C_3H_6$—Si(OCH$_3$)$_3$ or —$C_3H_6$—Si(OC$_2$H$_5$)$_3$; (ii) $A_2$ is represented by H; and (iii) $R_4$ is present and is represented by —$CH_2$—. In yet a further refinement of the compound of Structure I or II, (i) $A_1$ is represented by —$C_3H_6$—Si(OCH$_3$)$_3$ or —$C_3H_6$—Si(OC$_2$H$_5$)$_3$; (ii) $A_2$ is represented by —$C_3H_6$—Si(OCH$_3$)$_3$ or —$C_3H_6$—Si(OC$_2$H$_5$)$_3$; and (iii) $R_4$ is present and is represented by —$CH_2$—.

The hydrocarbon groups/moieties in the various components of the curable polyepoxysilane compound of Structure I or II generally can include saturated or unsaturated, linear or branched aliphatic hydrocarbon groups, alicyclic hydrocarbon groups, aryl hydrocarbon groups, and heteroatom-including analogs/derivates of the same (e.g., including N, O, S heteroatoms). The hydrocarbon groups (R, $R_1$, $R_2$, $R_3$, or $R_4$) additionally can include hydrolysable silyl groups (i.e., in addition to those explicitly illustrated in $A_1$ and $A_2$). As noted above, the hydrolysable X groups can be the same in all instances in the curable polyepoxysilane compound to promote uniform hydrolysis and condensation rates, but they can be different in alternate embodiments.

The disclosed curable polyepoxysilane compound has a high reactivity (e.g., promoting rapid and extensive curing), a robust chemical structure (e.g., providing resistance to degradation), and excellent mechanical properties once cured (e.g., in the form of a film on a substrate). The specific chemical structure and functional groups of the curable polyepoxysilane compound can be selected and synthesized by reaction between one or more aminosilanes (e.g., aminoalkyl[mono-, di-, or tri-]alkoxysilanes) with one or more mono- and/or polyfunctional epoxide-containing organic or hydrocarbon compounds and oligomers/polymers thereof (e.g., mono-, di-, or tri-glycidyl-type ethers or other epoxide-/oxirane-functionalized hydrocarbon compounds), for example in equivalent (molar) proportions based on the amino and epoxide functional groups, to yield polyepoxysilane compounds. Thus, the hydrocarbon moiety of the polyepoxysilane compound has a structure corresponding to a reaction product resulting from an amination reaction of the epoxide (e.g., mono-functional epoxide or poly-functional epoxide) with the aminosilane.

Suitable aminosilanes useable as a precursor to the hydrolysable silyl groups of the curable polyepoxysilane compound include any organic compound having one or more amine groups (e.g., free primary or secondary amino group) and one or more hydrolysable silyl groups per molecule (e.g., 1, 2, 3, 4, 5, or 6 hydrolysable silyl groups with 1 or 2 corresponding silicon atoms). The aminosilanes are suitably monoamines. The aminosilanes can have a hydrocarbon group having at least 1 or 2 and/or up to 6 or 10 carbon atoms that links the amino group with the hydrolysable silyl groups (e.g., with the amino group and the corresponding silicon atom at opposing terminal ends of the linking group). Suitable aminosilanes can be represented by the form $NHA_1A_2$, where $A_1$-$A_2$, X, and $R_1$-$R_4$ are as described above for the curable polyepoxysilane compound. Specific examples of suitable aminosilanes include (3-aminopropyl) trialkoxysilane (e.g., including trimethoxy (APTMS) and triethoxy (APTES) species) and bis(3-trialkoxysilylpropyl) amine (e.g., including trimethoxy (BTMSPA) and triethoxy (BTESPA) species).

Suitable epoxide-containing hydrocarbon compounds include glycidyl ethers of various hydrocarbon and heteroatom-substituted hydrocarbon groups, including saturated or unsaturated, linear or branched aliphatic hydrocarbon groups, alicyclic hydrocarbon groups, aryl/aromatic hydrocarbon groups, and heteroatom-including analogs/derivatives of the same (e.g., including N, O, S heteroatoms). In a refinement, the glycidyl-hydrocarbon ether is represented by

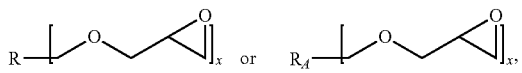

where R is generally a hydrocarbon or heteroatom-substituted hydrocarbon moiety (e.g., containing from 1 to 50 carbon atoms) and $R_A$ is more particularly an aromatic hydrocarbon moiety including one or more aromatic hydrocarbon groups (e.g., as described below). The functionality x of the glycidyl-hydrocarbon ether is at least one (e.g., x is 1, 2, 3, or 4, for example at least 1, 2, 3, or 4 and/or up to 6, 8, 10, 12, or 20). Alternatively or additionally, the hydrocarbon moiety includes one or more aromatic hydrocarbon groups, for example $C_6$-substituted or unsubstituted aromatic groups such as substituted or unsubstituted phenolic residues or ethers thereof (such as present in a glycidyl- or other epoxide-functional phenolic ether precursor to the curable polyepoxysilane compound). As representative examples, the aromatic hydrocarbon groups can include any of a variety of bisphenol-based moieties represented by $R_B$-[-Ph]$_2$, where $R_B$ is a hydrocarbon or heteroatom-substituted hydrocarbon linking group (such as having 1 to 50 carbons) between two Ph groups representing phenolic residues or ethers thereof. Representative (aromatic)bisphenol moieties includes derived from any commonly known bisphenol compound, such as bisphenol A, AP, AF, B, BP, C (cresol-based), C (chlorinated), E, F, G, M, S, P, PH, TMC, and/or Z. The hydrocarbon moiety additionally can include a plurality of aromatic hydrocarbon groups such as from bisphenol-based oligomers or polymers (e.g., having a plurality of $C_6$ aromatic groups as part of the backbone and/or as pendent groups, such as part of an aromatic/aliphatic polyether in a bisphenol-diglycidyl ether epoxy resin/prepolymer for silane functionalization to form the curable polyepoxysilane compound) or other phenol-based resins such as phenol-formaldehyde resins. An example di-functional epoxide-containing compound includes diglycidyl ether of bisphenol-A (DGEBA) (also known as liquid epoxy resin); example mono-functional epoxide-containing compounds include glycidoxypropyl trimethoxy silane (GPTMS), glycidoxypropyl triethoxy silane (GPTES), and glycidyl ether of para-tertiary butyl phenol (GEPTBP).

Figure 2:
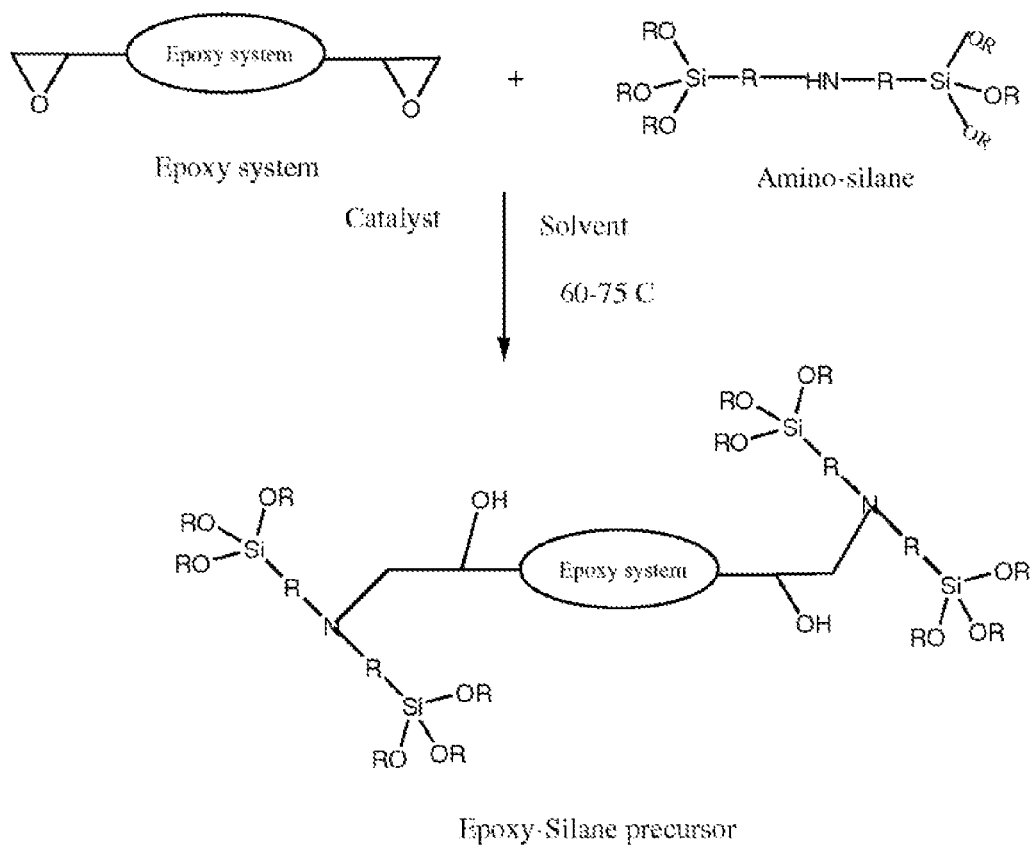
FIG. 2 illustrates a reaction scheme for the formation of a curable polyepoxysilane precursor (epoxy silane) for sol-gel coatings according to the disclosure.

FIG. 2 illustrates a general reaction scheme for forming a curable polyepoxysilane compound according to the disclosure. In the illustrated example, a generic di-functional epoxide-containing hydrocarbon compound (epoxy system) is reacted with a generic bis(trialkoxysilylalkyl)amine(aminosilane) to form a curable polyepoxysilane compound (epoxy-silane precursor) having two epoxy groups (—CH (OH)—CH$_2$— or —CH$_2$—CH(OH)—) and 12 hydrolysable silyl alkoxy groups (Si—OR). When the epoxide-containing hydrocarbon is, for example, DGEBA (shown in FIG. 1), the generically illustrated core of the epoxy system and curable polyepoxysilane compound corresponds to the bisphenol-A core group of DGEBA.

Curing Process

The curable polyepoxysilane compound in any of the various embodiments of the disclosure can be cured with water to form a cured polyepoxysilane compound having covalent intermolecular siloxane crosslinks in the networked polymer product. The intermolecular crosslinks relate to the formation of covalent bonds between originally separate curable polyepoxysilane molecules. In some instances, intramolecular crosslinking is possible in the networked polymer product as well. The curing process generally involves a serial, two-step mechanism in which at least some of the hydrolysable silyl groups in the curable polyepoxysilane compound are first hydrolyzed to silanol groups (e.g., generally an acid-catalyzed aqueous reaction), and the silanol groups are then condensed to form intermolecular siloxane crosslinks. Condensation/crosslinking to form a siloxane link can occur between two silanol groups (e.g., to yield water as a byproduct) or between a silanol group and an unhydrolyzed silyl group from the curable polyepoxysilane compound (e.g., to yield a corresponding alcohol from an alkoxy hydrolysable group or a corresponding acid form a halogen hydrolysable group). The resulting networked polymer includes a silica network sol with individual units linked via the epoxy-containing hydrocarbon moiety of the curable polyepoxysilane compound (e.g., including siloxane cage-like structures).

In an extension of the curing process that further involves the coating of the polyepoxysilane compound onto a substrate, the curable polyepoxysilane compound is first partially cured (e.g., partially, substantially, or completely hydrolyzed but without partial, substantial, or complete condensation) in the absence of the substrate. The partially cured polyepoxysilane compound is then applied to the substrate by any convenient means (e.g., dipping, immersing, spraying, coating, etc. the substrate with a solution/mixture including the partially cured polyepoxysilane compound). Once applied, the partially cured polyepoxysilane compound on the substrate continues to cure (e.g., including further hydrolysis where appropriate as well as condensation for network polymer formation), thereby forming the cured polyepoxysilane compound as a coating on the substrate. Once applied to the substrate and after substantial evaporation of water and any organic solvent, a rapid and high degree of condensation is desirable to obtain films with good barrier properties. The rates of such gel-formation reactions are a function of temperature, among other factors. Suitably, the post-application cure can be performed at ambient temperature (e.g., 20° C. to 30° C.) or at higher temperatures (e.g., ambient temperature up to 50° C., 75° C., 100° C., 150° C., or 200° C.).

In a general curing process according to the disclosure, the curable polyepoxysilane compound is initially hydrolyzed to form a silanol analog to the curable polyepoxysilane compound (e.g., where some, most, or all of the hydrolysable silyl groups are replaced by silanol —OH; at least 50%, 60%, 70% or 80% and/or up to 80%, 90%, 95% or 100% on a number or molar basis are hydrolyzed), and the silanol groups then condense to form intermolecular cross-links in a networked polymer product. The silanol analog can be represented by the above Structure I or II, where some, most, or all of the hydrolysable groups X are replaced by —OH. As described in more detail below, the curable polyepoxysilane compound is suitably at least partially hydrolyzed prior to coating or other contact with an intended substrate (e.g., an aluminum or aluminum alloy). After an initial pre-hydrolysis period (or induction period) prior to substrate contact, the (partially) hydrolyzed polyepoxysilane compound continues to hydrolyze and condense on the substrate to form an adherent polymer coating.

It is desirable increase the relative silanol content of a coating solution (sol) including the polyepoxysilane compound before application onto the substrate in order to achieve a resulting coating with good barrier properties. The rate of hydrolysis for different sol-gel precursors (i.e., curable polyepoxysilane compounds) can significantly vary under given reaction conditions, so systems containing two or more precursors of different reactivity (e.g., whether different compounds altogether or analogous precursors with different hydrolysable groups) can result in a broad distribution of species at various points in the curing reaction path. For example, excessive hydrolysis and condensation can be observed in the more reactive precursor species, while little to no hydrolysis and/or condensation may be observed in the less reactive precursor species. A relatively low silanol content can result in lower a number of covalent bonds with a metal substrate, thus forming a coating with reduced corrosion resistance and substrate adhesion. The curable polyepoxysilane compound suitably has 3 or more (e.g., 3, 4, 6, 9, 12, 18, or 24) hydrolysable silyl groups of the same type (e.g., methoxy or ethoxy). The polyepoxysilane compound, when hydrolyzed in aqueous acidic solution, exhibits a fairly uniform, rapid rate of hydrolysis (e.g., compared to a metal alkoxide or silicon tetraalkoxide such as TEOS). The high functionality of the polyepoxysilane compound helps produce a denser film, and the absence of metal or silicon alkoxide in some embodiments makes possible a single step and faster process. The curable polyepoxysilane compound and related induction/coating/curing process provides improved control over the composition of the coating bath solution (e.g., in terms of relative silanol content) and hence the performance/properties of the corresponding pretreatments and coatings. For example, the curable polyepoxysilane compound in the initial reaction mixture is suitably pre-hydrolyzed for a sufficient time during an induction period such that least 50%, 60%, 70%, or 80% and/or up to 80%, 90%, 95%, or 100% of the original hydrolysable silyl groups (number or molar basis) have been hydrolyzed to silanol groups. Alternatively or additionally, the induction time can be selected to avoid excessive condensation, such that not more than 5%, 10%, 20%, or 30% of the original hydrolysable silyl groups (number or molar basis) have been condensed to siloxane linking groups.

The curable polyepoxysilane compound is suitably provided in the form of an aqueous mixture that serves as an initial pre-hydrolysis (induction) medium as well as a coating/dipping solution for subsequent substrate application. In addition to water and the curable polyepoxysilane compound, the aqueous mixture can further include an organic solvent for the curable polyepoxysilane compound, a (hydrolysis) catalyst, a corrosion inhibitor, and a silane crosslinker. Suitable amounts for the various mixture components relative to the mixture as a whole can include: at least 5 wt. % or 10 wt. % and/or up to 30 wt. % or 40 wt. % for the curable polyepoxysilane compound, at least 2 wt. % or 10 wt. % and/or up to 50 wt. % or 70 wt. % for water, at least 10 wt. % or 20 wt. % and/or up to 50 wt. % or 50 wt. % for the organic solvent, at least 0.5 wt. % or 1 wt. % and/or up to 3 wt. % or 5 wt. % for the catalyst, and at least 0.1 wt. % or 1 wt. % and/or up to 3 wt. % or 5 wt. % for the corrosion inhibitor (when present). Alternatively or additionally, the corrosion inhibitor can be present in an amount such that its concentration in the final cured film is at least 0.1 wt. %, 0.5 wt. %, or 1 wt. % and/or up to 3 wt. %, 5 wt. %, or 10 wt. %.

In some embodiments, the curable polyepoxysilane compound (e.g., as a composition generally or as added to the aqueous induction medium/application bath) can be a single chemical species. In other embodiments, the curable polyepoxysilane compound (e.g., as a composition generally or as added to the aqueous induction medium/application bath) can be a mixture of multiple chemical species. In a refinement, the curable polyepoxysilane compound is a blend including a first curable polyepoxysilane compound having a first number of hydrolysable silyl groups and a second curable polyepoxysilane compound having a second number of hydrolysable silyl groups. Suitably, the first and second numbers of hydrolysable silyl groups are different (e.g., where the first number of hydrolysable silyl groups is less than the second number of hydrolysable silyl groups, or vice versa). Different numbers of hydrolysable silyl groups can improve the stability of aqueous induction medium when the blend of first and second curable polyepoxysilane compounds is added to the medium. For example, the first number of hydrolysable silyl groups can range from 3 to 9 (e.g., at least 3, 4, or 6 and/or up to 6 or 9), which suitably can result when forming the first curable polyepoxysilane compound from a hydrocarbon moiety precursor having a single epoxide group. Alternatively or additionally, the second number of hydrolysable silyl groups can range from 6 or 9 to 24 (e.g., at least 6, 9, or 12 and/or up to 12, 18, or 24), which suitably can result when forming the second curable polyepoxysilane compound from a hydrocarbon moiety precursor having a two or more epoxide groups.

The addition of a water-miscible organic solvent that is compatible (e.g., capable of solvating) the curable polyepoxysilane compound can provide sufficient phase stability to the mixture and can control the equilibrium reaction rates in the curing system. The water/solvent ratio in the mixture can be selected to control the properties of the resulting coating. The solvent is suitably an alcohol such as methanol, ethanol, (iso)propanol, and mixtures thereof. The particular alcohol solvent can be selected to correspond to the alcohol that is liberated from the curable polyepoxysilane compound upon hydrolysis (e.g., an alcohol corresponding to the alkoxy group on the silicon atom). Other non-alcohol solvents that are water-miscible and compatible with the polyepoxysilane precursor also can be used, for example including acetone and/or tetrahydrofuran (THF).

The catalyst added to the mixture is suitably a Bronsted acid, for example a carboxylic acid such as formic acid, acetic acid, and/or lactic acid. Alternatively or additionally, stronger mineral acids such as phosphoric acid, nitric acid, and/or hydrochloric acid can be used. The catalyst suitably is added to the mixture in an amount to achieve an acidic pH value to be maintained during induction/coating, for example of at least 2 or 3 and/or up to about 4, 5, or 6.

The corrosion inhibitor added to the mixture can be any suitable compound known for its corrosion-resistance and/or antioxidant properties. The presence of the corrosion inhibitor in the curing mixture allows the inhibitor to be homogeneously dispersed in the eventual cured polyepoxysilane coating. In some embodiments, organic inhibitors are preferred over inorganic ones, as they generally have little or effect on the pH of the curing mixture, and it is desirable to carefully control the pH value in order to control the kinetics of the hydrolysis and condensation reactions in the mixture. Suitable organic inhibitors include heterocyclic organic compounds having 4 to 20 carbon atoms and one or more heteroatoms (e.g., N, O, S) along with anti-corrosion properties. Specific examples of suitable organic inhibitors include 8-hydroxyquinoline, benzimidazole, mercaptobenzothiazole, mercaptobenzimidazole, benzotriazole, and combinations thereof.

In some embodiments, the curable polyepoxysilane compound (e.g., a single species of the curable polyepoxysilane compound or multiple different species of curable polyepoxysilane compounds) is the only source of intermolecular siloxane crosslinks in the reaction mixture and in the resulting cured polyepoxysilane compound (e.g., the reaction mixture is free or substantially free from other added species having hydrolysable silyl groups). As described above, it can be desirable to have only a single chemical species in the mixture that contains hydrolysable silyl groups to promote uniformity of the curing reactions in the system. Alternatively or additionally, the mixture can be free from other added sources of silicon, whether in the form of hydrolysable silyl groups, cured siloxane crosslinks, or otherwise. In other embodiments, however, the reaction mixture can include a silane crosslinker to increase the crosslink density and barrier properties in the resulting cured polymer coating. Suitable silane crosslinkers can be represented by the form $Si(R_3)_{4-y}X_y$, where X and $R_3$ are as described above for the curable polyepoxysilane compound, except that y is selected to be 2, 3, or 4. Examples of suitable silane crosslinkers include tetraethoxyorthosilicate (TEOS) and tetramethoxyorthosilicate (TMOS). Because of the generally differing rates of hydrolysis between the silane crosslinker and the curable polyepoxysilane compound, the silane crosslinker is suitably pre-hydrolyzed to a desired degree in a separate aqueous reaction mixture (i.e., which does not contain the curable polyepoxysilane compound), and then the (partially) hydrolyzed silane crosslinker is added to the reaction mixture containing the curable polyepoxysilane compound for its pre-hydrolysis (induction) period. While the inclusion of the silane crosslinker generally involves an initial reaction/process step, it can provide a resulting cured polyepoxysilane compound with improved structural properties.

Coated Article

Figure 4:
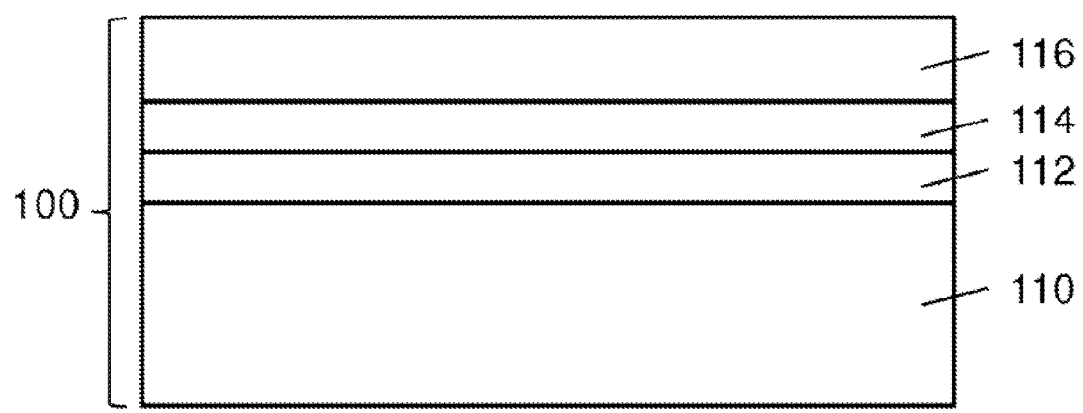
FIG. 4 illustrates a coated article with a cured polyepoxysilane compound coating according to the disclosure.

FIG. 4 illustrates a coated article 100 according to the disclosure. The coated article 100 includes a substrate 110 having a cured polyepoxysilane compound as a coating 112 on a surface (e.g., outer surface) of the substrate 110. The cured coating (e.g., as formed by the above method) suitably has a thickness ranging from 1 µm or 2 µm to 5 µm or 10 µm for a single coating application, and multiple coatings applied/cured in series can form a correspondingly thicker coating 112 if desired.

The substrate 110 is not particularly limited, but it is suitably a metallic substrate 110. In this case, the cured polyepoxysilane compound coating 112 serves to reduce or prevent corrosion of the underlying metallic substrate 110 from ambient environmental conditions. In various embodiments, the substrate can be a metal (e.g., aluminum), a metal alloy (e.g., an aluminum-containing alloy), or a non-metal. In some embodiments, the polyepoxysilane coating 112 is adhered to the substrate via covalent linkages. Many metal substrates (M), including aluminum (Al), contain surface-bound hydroxyl groups (e.g., M-OH or Al—OH, either present natively or after surface preparation by conventional techniques) that themselves can condense during cure with silanol groups in the hydrolyzed polyepoxysilane compound to release water and form an adherent, covalent linking functional group between the metal substrate and the cured polyepoxysilane compound (e.g., [polymer coating]-SiOM-[metal substrate] or [polymer coating]-SiOAl-[aluminum substrate]).

In an extension, the coated article 100 optionally can include a polymeric primer 114 layer and/or a polymeric topcoat 116 layer as additional layers providing barrier/sealant/anti-corrosion properties. As illustrated in FIG. 4, the primer layer 114 is coated on an outer surface of the polyepoxysilane coating 112 (e.g., the surface opposing that to which the substrate 110 is adhered). Similarly, the topcoat layer 116 is coated on an outer surface of the primer layer 114 (e.g., the surface opposing that to which the polyepoxysilane coating 112 is adhered). When the primer layer 114 is not present, the topcoat layer 116 can be coated on the outer surface of the polyepoxysilane coating 112). In addition to providing anti-corrosion properties, the polymeric primer layer 114 additionally promotes adhesion between the polyepoxysilane coating 112 and the topcoat layer 116. Such polymeric coatings are suitably chromium-free (e.g., free from hexavalent chromium, trivalent chromium, and/or chromium in any other form). Suitable polymeric materials for the primer and topcoat are generally known and are not particularly limited, with specific examples including epoxy-, polyester-, polyurethane-, polyurea-, and acrylic-based coatings (e.g., where the primer and topcoat suitably have the same or similar base polymeric character, such as epoxy-based primers/topcoats having hydrogen-bonding donor/acceptor groups for improved wetting and adhesion properties relative to the epoxy groups of the cured polyepoxysilane coating).

Mannari U.S. Publication No. 2012/0258319, incorporated by reference herein in its entirety, provides additional disclosure related to hydrolysable and condensable silane compositions, silane precursors useful for forming the same, and cured coatings (e.g., coated substrate articles) formed from the same.

EXAMPLES

The following examples illustrate the disclosed processes and compositions, but are not intended to limit the scope of any claims thereto.

Examples 1-3

These examples illustrate the formation of a curable polyepoxysilane compound according to the disclosure. The curable precursor compound was applied to an aluminum test substrate, cured to form a sol-gel coating on the substrate, and then tested for its anti-corrosion properties. Polyureasil coatings according to Mannari U.S. Publication No. 2012/0258319 were formed as comparative test compositions.

Preparation of curable polyepoxysilane precursors: Curable polyepoxysilane precursors were formed by first dissolving an epoxide compound (resin) in a suitable solvent such as anhydrous ethyl alcohol or its blend with aromatic hydrocarbon in a reaction flask under mechanical stirring. Comparative curable polyureasil precursors were similarly formed by first dissolving an isocyanate compound in the solvent. The reaction mixture was heated to 60° C. and an aminosilane compound was added to the mixture within 10-20 min. For each equivalent of epoxide group, 0.9 amine-H equivalents of aminosilanes were added. The temperature was adjusted to 55-60° C. and the reaction continued until the epoxide group content was less than 0.1%. The amine value was also determined to confirm the completion of reaction. Nitrogen gas was purged continuously during synthesis to keep inert atmosphere. The reaction products were adjusted to 60% non-volatile content using anhydrous ethanol (although other solvents could be used) and stored in a dry environment.

The specific curable precursor compounds formed in the examples include: (Example 1) a comparative bis-ureasil with low silane content (reaction of IPDI+APTMS, (Example 2) a comparative bis-ureasil with high silane content (reaction of IPDI+BPMSPA), and (Example 3) a curable polyepoxysilane (or epoxy silane) with high silane content (reaction of DGEBA+BTMSPA). A representative reaction scheme for the formation of the curable polyepoxysilane precursor is shown in FIG. 2.

Preparation of sol-gel bath and application of coatings (pretreatment): An application bath (preparing sol) was prepared by adding each curable precursor solution into a mixture containing deionized water and ethyl alcohol. The mixture was adjusted to a pH value ranging from about 3.5 to 4.5 using glacial acetic acid. The bath was stirred for 30 min before application of coatings (i.e., hydrolyzing at least some of the alkoxy silane groups to condensable silanol groups).

The coatings were applied by using a dip-coating apparatus to apply the (hydrolyzed) curable precursor compounds to aluminum alloy test substrates (alloy AA 2024-T3 including primarily Al, about 3.8-4.9 wt. % Cu, about 1.2-1.8 wt. % Mg, and minor amounts of Si, Fe, Mn, Cr, Zn, and/or Ti; alloy AA 2024-T3 is the most prone to corrosion of aluminum alloys in Examples 1-9). The preparation (cleaning) of sample panels (of aluminum alloys) and application parameters were as described in the examples of Mannari U.S. Publication No. 2012/0258319. After application, samples were allowed to stand for 15 minutes (flash-off time), followed by curing in an oven at 100° C. to 160° C., generally for about 30 min. Other samples were cured at room temperature for 48 hrs (results not shown).

Evaluation of corrosion resistance properties: The coated aluminum test panels were tested for corrosion resistance properties using (1) DC polarization (an electrochemical method for corrosion study) and (2) the ASTM B117 neutral salt-fog test (incorporated herein by reference; commonly used for assessment of corrosion resistance as an accelerated corrosion test).

Figure 3:
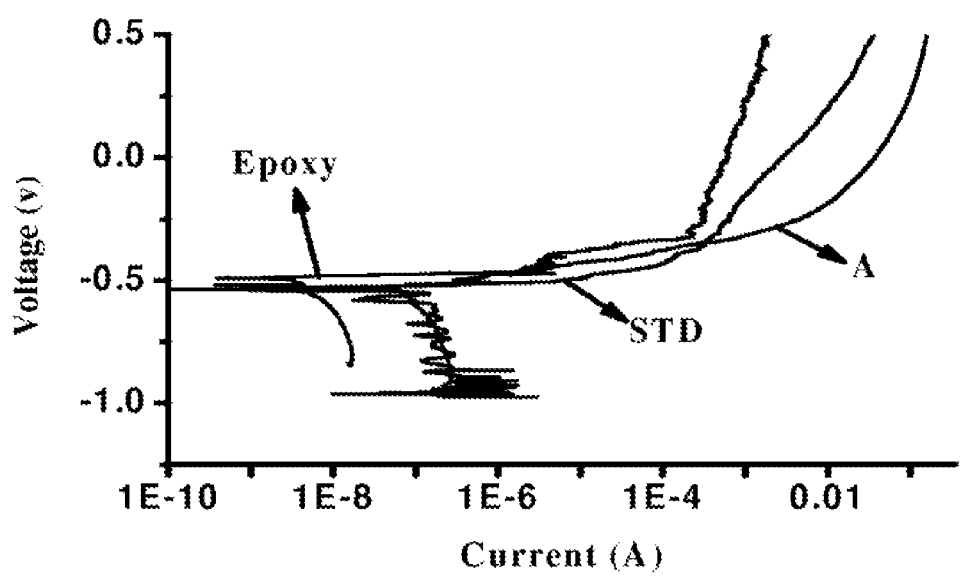
FIG. 3 is a graph illustrating the DC polarization corrosion resistance properties of a cured polyepoxysilane coating according to the disclosure and comparative cured polyureasil coatings.

The DC polarization results are shown in FIG. 3 (voltage vs. current) and Table 1 below. As can be seen from these data, the cured epoxy-silane coating has a corrosion current ($I_{curr}$) that is about an order of magnitude lower than the bis-ureasil system with comparable silane functionality and about two orders of magnitude lower than the low silane bis-ureasil system disclosed earlier. Similarly, the corrosion rate (CR), which calculates loss of a layer thickness of metal due to corrosion per year, is also order or two of magnitude lower compared with the bis-ureasil systems.

TABLE 1

DC Polarization Results

| Property | Bis-Ureasil (low silane) Example 1 | Bis-Ureasil (high silane) Example 2 | Epoxy Silane (high silane) Example 3 |
|---|---|---|---|
| $E_{corr}$ (mV) | −550 | −535 | −536 |
| $I_{corr}$ (mA/cm$^2$) | $1.1 \times 10^{-5}$ | $6.6 \times 10^{-6}$ | $6.9 \times 10^{-7}$ |
| CR (mm/year) | $1.8 \times 10^{-4}$ | $7.5 \times 10^{-5}$ | $7.5 \times 10^{-6}$ |

The neutral salt-fog test results for all three coatings are shown in Table 2 below. As can be seen from Table 2, at the end of 500 hr exposure, the epoxy-silane system showed better performance. Visual inspection of the exposed panels at various times during the test further demonstrated the improved corrosion resistance of the epoxy-silane system coating.

TABLE 2

Accelerated Salt-Fog Test Results

| Ex. | Coating | Rating | | 0 hr | 100 hr | 300 hr | 500 hr |
|---|---|---|---|---|---|---|---|
| 1 | Bis-Ureasil (low silane) | D610 | Distribution Rating | 10 | 8S9G9P 8 | 7S8G8P 7 | 4S6G4P 4 |
| 2 | Bis-Ureasil (high silane) | D610 | Distribution Rating | 10 | 10 | 9S9G9P 9 | 5S9G9P 5 |
| 3 | Epoxy-Silane (high silane) | D610 | Distribution Rating | 10 | 10 | 9S9G9P 9 | 8S9G8P 8 |

Without being bound to any particular theory, it is believed that the combination of the silane functionality and the backbone structure of the silane precursor (epoxy backbone) contribute to the improved corrosion resistance properties. It is important to note that, in the curable polyepoxysilane precursor (generically denoted as an epoxy-silane precursor), there is no epoxide functionality (i.e., essentially no cyclic oxirane/ethylene oxide groups). The epoxide groups originally present in the hydrocarbon compounds used to form the polyepoxysilane precursor and eventual backbone of the cured network polymer react with the functionalized silanes (e.g., amino silanes as in the examples) to form epoxy linking groups between the hydrocarbon (e.g., aromatic hydrocarbon) core and the terminal alkoxysilane groups of the curable polyepoxysilane precursor. Thus, "epoxy" as used herein represents a ring-opened reaction product of a cyclic epoxide group with a functionalized silane (e.g., —CH$_2$—CH(OH)—, such as [silane]—CH$_2$—CH(OH)-[hydrocarbon core] or [hydrocarbon core]—CH$_2$—CH(OH)-[silane] as schematically illustrated in FIG. 2). The disclosed epoxy-silanes, in particular those based on (bis)phenolic resins/precursors, can have a backbone structure containing rigid aromatic structures and a general absence of polar groups, thus lessening the ability of the cured coating to absorb ambient moisture (i.e., which can contribute to the corrosion of an underlying substrate) and improving performance in corrosion resistance. For example, the polymeric backbone resulting from bisphenol or other aromatic precursors consists substantially/essentially of aromatic hydrocarbon units (e.g., phenolic ether units derived from bisphenol) and aliphatic hydrocarbon units (e.g., linking groups between aromatic hydrocarbon units and/or linking groups to hydrolysable silyl groups or condensed siloxane groups). Polar character due to the —OH groups resulting from the epoxide ring opening is thought to be small and not a significant contribution to water absorption, creating a condensed network polymer that is substantially hydrophobic/water-resistant nature.

Examples 4-6

In Examples 4-5, curable polyepoxysilane compounds with high silane content (reaction of DGEBA+BTMSPA as above for Example 3) were formed, coated onto aluminum alloy test panels (alloy AA 6022 including primarily Al, about 0.8-1.5 wt. % Si, about 0.45-0.7 wt. % Mg, and minor amounts of Fe, Cu, Mn, Cr, Zn, and/or Ti), and cured in the manner described above for Examples 1-3. A corrosion inhibitor was added to the sol-gel bath: benzotriazole (Example 4; 3 wt. % relative to curable polyepoxysilane compounds) or chromium nitrate (Example 5; 0.5 wt. % relative to curable polyepoxysilane compounds). For Example 6, a commercial hexavalent chromate pretreatment (ALODINE 1200S pretreatment coating; available from Henkel, Germany) was applied to an aluminum alloy test panel. The test panels were then tested for corrosion resistance properties using (1) DC polarization and (2) the ASTM B117 neutral salt-fog test as above for Examples 1-3. The results are shown in Table 3 below. As indicated in Table 3, the cured polyepoxysilane compound coatings exhibit good barrier properties and comparable corrosion resistance relative to conventional hexavalent chromium pretreatments.

TABLE 3

DC Polarization and Salt Fog Results

| Property | Epoxy Silane (benzotriazole) Example 4 | Epoxy Silane (chromium nitrate) Example 5 | Conventional Chromate Treatment Example 6 |
|---|---|---|---|
| $E_{corr}$ (mV) | −1303 | −1090 | −1038 |
| $I_{corr}$ (A/cm$^2$) | $2.6 \times 10^{-7}$ | $3.2 \times 10^{-7}$ | $9.7 \times 10^{-7}$ |
| Salt Fog Rating (500 hr) | 9P | 10P | 10P |

Examples 7-9

In Example 3, a bi-functional epoxide (DGEBA) was reacted with a hexa-functional aminosilane (BTMSPA) to form a curable polyepoxysilane compound with 12 hydrolysable silyl groups. Curable polyepoxysilane compounds with lower silane functionality were formed in a manner similar to Example 3, but instead using mono-functional epoxide compounds reacted with tri- and hexa-functional aminosilanes including 3-(aminopropyl)triethoxy (or methoxy) silane, bis(3-trimethoxysilyl-propyl)amine, and bis(3-triethoxysilyl-propyl)amine. The mono-functional epoxy compounds used were: glycidyl ether of para-tertiary butyl phenol (GEPTBP), glycidoxypropyl trimethoxy silane (GPTMS), and glycidoxypropyl triethoxy silane (GPTES). As a result, curable polyepoxysilane compounds with 3, 6, or 9 hydrolysable silyl groups were formed and could be used reduce and control the average silane functionality relative to the 12 hydrolysable silyl groups in Example 3. It was found that stability of the sol-gel bath prepared from combination of these precursors (i.e., a reduced silane-functionality curable polyepoxysilane compound formed from the mono-functional epoxide in combination with the curable polyepoxysilane compound including 12 silyl groups formed from the bi-functional epoxide) showed significantly improved bath stability time, increasing from about 2-3 hours (Example 3) to 24 hours. Further, the corrosion resistance properties were comparable to those based on only the bi-functional epoxide systems.

In Examples 7-8, curable polyepoxysilane compounds with reduced silane content formed were formed as above for Example 3, except that a blend of mono-functional and di-functional epoxides (GEPTBP and DGEBA, respectively) was reacted with a hexa-functional aminosilane (BTMSPA) to form a curable polyepoxysilane compound blend, with some curable polyepoxysilanes having 6 hydrolysable silyl groups (i.e., GEPTBP+BTMSPA product) and some curable polyepoxysilanes having 12 hydrolysable silyl groups (i.e., DGEBA+BTMSPA product). The blend of functional epoxides included about 75% DGEBA and 25% GEPTBP on an epoxide-equivalent basis (i.e., about 60 mol. % DGEBA and 40 mol. % GEPTBP). An application bath (sol-gel bath) was prepared by adding the curable polyepoxysilane compound blend (about 10-20 wt. % in the bath) into a mixture containing deionized water and ethyl alcohol (about 1:2 to 1:1 by volume). The mixture was adjusted to a pH value ranging from about 3 to 4 using glacial acetic acid as a catalyst. For Example 7, no corrosion inhibitor was added to the sol-gel bath. For Example 8, mercaptobenzothiazole (MBT) as a corrosion inhibitor as was added to the sol-gel bath (about 3 wt. % relative to curable polyepoxysilane compounds).

Aluminum alloy test panels (alloy AA-3003-H14 including primarily Al, about 0.05-0.2 wt. % Cu, about 1.0-1.5 wt. % Mn, and minor amounts of Si, Fe, and/or Zn) were degreased and chemically etched before application of sol-gel coatings. All coatings were applied at room temperature (about 25-30° C.) using an automatic dip coater (PTL-200, MTI Corporation), at a withdrawal speed of about 15-17 cm/minute, with a residence time of about 15-20 seconds. After application, the panels were placed vertically in a panel stacker for 15 minutes of air drying, followed by 30 minutes of thermal curing in an air circulating oven at 120° C. The typical dry-film thickness of coatings was about 5-7 micron. The test panels were then tested for corrosion resistance properties using DC polarization as above for Examples 1-3. The results are shown in Table 4 below for Examples 7-8 along with an untreated aluminum alloy test panel control (Example 9). Salt-fog test results (not shown) also corroborated well with the DC polarization results.

TABLE 4

DC Polarization Results

| Property | Reduced Silane Blend (no MBT) Example 7 | Reduced Silane Blend (MBT) Example 8 | Untreated Aluminum Panel Example 9 |
|---|---|---|---|
| $E_{corr}$ (mV) | −734 | −721 | −662 |
| $I_{corr}$ (A/Cm$^2$) | $1.0 \times 10^{-7}$ | $3.6 \times 10^{-9}$ | $1.5 \times 10^{-6}$ |
| Corrosion Inhibition Efficiency (rel. to Ex. 9) | 93.4% | 99.7% | n/a |

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed is:

1. A curable polyepoxysilane compound comprising:
a compound having the formula

R—[—O—R$_4$—CH(OH)—CH$_2$—NA$_1$A$_2$]$_x$; (1)

wherein:
(i) R is selected from the group consisting of linear aliphatic, branched aliphatic, and alicyclic hydrocarbons containing from 8 to 50 carbon atoms when x is 2 or from 4 to 50 carbon atoms when x is 3 or 4, the hydrocarbons being free from aromatic moieties;
(ii) A$_1$ is represented by —R$_1$—Si(R$_3$)$_{3-y}$X$_y$;
(iii) A$_2$ is represented by —R$_2$—Si(R$_3$)$_{3-z}$X$_z$ or H or R$_3$;
(iv) X is a hydrolysable group independently selected from the group consisting of alkoxy groups, aryloxy groups, carboxyloxy groups, and halogens;
(v) R$_1$ and R$_2$ are independently selected from the group consisting of hydrocarbons containing from 1 to 20 carbon atoms and heteroatom-substituted hydrocarbons containing from 1 to 20 carbon atoms;
(vi) R$_3$ is independently selected from the group consisting of H, hydrocarbons containing from 1 to 20 carbon atoms, and heteroatom-substituted hydrocarbons containing from 1 to 20 carbon atoms;
(vii) R$_4$ is either (A) absent or (B) selected from the group consisting of hydrocarbons containing from 1 to 20 carbon atoms and heteroatom-substituted hydrocarbons containing from 1 to 20 carbon atoms;
(viii) x is 2, 3, or 4;
(ix) y is 1, 2, or 3;
(x) z is 1, 2, or 3 when A$_2$ is not H or R$_3$; and
(xi) the number of hydrolysable groups X ranges from 9 to 24.

2. The compound of claim 1, wherein the hydrolysable groups X are alkoxy groups and are further independently selected from the group consisting of methoxy groups, ethoxy groups, propoxy groups, and isopropoxy groups.

3. The compound of claim 1, wherein:
(i) A$_1$ is represented by —C$_3$H$_6$—Si(OCH$_3$)$_3$ or —C$_3$H$_6$—Si(OC$_2$H$_5$)$_3$;
(ii) A$_2$ is represented by H; and
(iii) R$_4$ is present and is represented by —CH$_2$—.

4. The compound of claim 1, wherein:
(i) A$_1$ is represented by —C$_3$H$_6$—Si(OCH$_3$)$_3$ or —C$_3$H$_6$—Si(OC$_2$H$_5$)$_3$;
(ii) A$_2$ is represented by —C$_3$H$_6$—Si(OCH$_3$)$_3$ or —C$_3$H$_6$—Si(OC$_2$H$_5$)$_3$; and
(iii) R$_4$ is present and is represented by —CH$_2$—.

5. A process for curing a curable polyepoxysilane compound, the process comprising:
(a) providing a curable polyepoxysilane compound according to claim 1; and
(b) curing the curable polyepoxysilane compound with water, thereby hydrolyzing and condensing at least some of the hydrolysable silyl groups to form a cured polyepoxysilane compound comprising covalent intermolecular siloxane crosslinks in the cured polyepoxysilane compound.

6. The process of claim 5, wherein providing the curable polyepoxysilane compound in part (a) comprises providing a mixture comprising: (i) the curable polyepoxysilane compound, (ii) an organic solvent for the curable polyepoxysilane compound, (iii) water, (iv) a catalyst, (v) optionally a corrosion inhibitor; and (vi) optionally a silane crosslinker.

7. The process of claim 5, further comprising:
(c) applying partially cured polyepoxysilane compound from part (b) to a substrate; and
(d) further curing the partially cured polyepoxysilane compound on the substrate, thereby forming the cured polyepoxysilane compound as a coating on the substrate.

8. The process of claim 7, wherein the substrate is a metallic substrate and the cured polyepoxysilane compound coating reduces or prevents corrosion of the metallic substrate.

9. The process of claim 8, wherein the cured polyepoxysilane compound coating is covalently bonded to the metallic substrate via a —SiO— functional group.

10. The process of claim 8, wherein the metallic substrate comprises aluminum.

11. The process of claim 7, further comprising:
applying a polymeric primer as a coating on a surface of the cured polyepoxysilane compound opposite the substrate; and
applying a polymeric topcoat as a coating on a surface of the polymeric primer opposite the cured polyepoxysilane compound.

12. The compound of claim 1, wherein R contains 8 to 50 carbon atoms when x is 2, 3, or 4.

13. The compound of claim 1, wherein R is an alicyclic hydrocarbon.

* * * * *